United States Patent
Funda et al.

(10) Patent No.: US 10,888,538 B2
(45) Date of Patent: Jan. 12, 2021

(54) PUFA SALT FORMULATIONS (I)

(71) Applicant: DSM IP ASSETS B.V., Heerlen (NL)

(72) Inventors: Elger Funda, Kaiseraugst (CH); Denis Hug, Kaiseraugst (CH); Odile Krainz, Kaiseraugst (CH); Sean McDonnell, Kaiseraugst (CH); Shakuntala Ramnarain, Kaiseraugst (CH); Casey Sumner, Kaiseraugst (CH); Qiong Tang, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/468,512

(22) PCT Filed: Dec. 13, 2017

(86) PCT No.: PCT/EP2017/082551
§ 371 (c)(1),
(2) Date: Jun. 11, 2019

(87) PCT Pub. No.: WO2018/108975
PCT Pub. Date: Jun. 21, 2018

(65) Prior Publication Data
US 2020/0085773 A1    Mar. 19, 2020

(30) Foreign Application Priority Data
Dec. 13, 2016   (EP) .................... 16203602

(51) Int. Cl.
*A61K 31/202* (2006.01)
*A61K 9/16* (2006.01)

(52) U.S. Cl.
CPC .......... *A61K 31/202* (2013.01); *A61K 9/1658* (2013.01)

(58) Field of Classification Search
None
See application file for complete search history.

(56) References Cited

U.S. PATENT DOCUMENTS 5,853,761 A * 12/1998 Kumabe ............... A23L 3/3508
                                                             424/484
6,299,928 B1 * 10/2001 Takeuchi ............... A23K 40/10
                                                             426/656
2005/0184275 A1    8/2005 Mora-Gutierrez et al.

FOREIGN PATENT DOCUMENTS

| EP | 1 064 853 | 1/2001 |
| EP | 2 131 674 | 12/2009 |
| WO | 2016/049018 | 3/2016 |

OTHER PUBLICATIONS

International Search Report for PCT/EP2017/082551, dated Jan. 31, 2018, 4 pages.
Written Opinion of the ISA for PCT/EP2017/082551, dated Jan. 31, 2018, 8 pages.
Adamson et al, "Characterization of Multiply Phosphorylated Peptides Selectively Precipitated from a Pancreatic Casein Digest," Biochemistry and Molecular Biology Unit, Australia, 1995 J Dairy Sci 78:2653-2659.

* cited by examiner

*Primary Examiner* — Brian J Davis
(74) *Attorney, Agent, or Firm* — Nixon & Vanderhye P.C.

(57) ABSTRACT

The present patent application relates to novel polyunsaturated fatty acid salt (PUFA salts) solid formulations.

14 Claims, No Drawings

PUFA SALT FORMULATIONS (I)

This application is the U.S. national phase of International Application No. PCT/EP2017/082551 filed 13 Dec. 2017, which designated the U.S. and claims priority to EP Patent Application No. 16203602.4 filed 13 Dec. 2016, the entire contents of each of which are hereby incorporated by reference.

The present patent application relates to novel polyunsaturated fatty acid salt (PUFA salts) solid formulations.

Polyunsaturated fatty acids (PUFAs) are very well-known compounds for a healthy diet (especially the omega-3 fatty acids). The PUFAs (especially the omega-3 fatty acids) have variety of health benefits against for example cardiovascular diseases (CVDs) including well-established hypotriglyceridemic and against anti-inflammatory effects.

Therefore, PUFAs are important ingredients in a healthy diet (for animals and humans).

PUFAs can be found in a variety of plants and animal in various quantities and in various mixtures (of the different PUFA).

A very good source of omega-3 fatty acids are for example fish.

However, it is also possible to produce PUFAs synthetically.

Since many consumers do not like fish, especially the smell and taste of it, (or other PUFA containing sources), it is very common to add PUFAs to other dietary products (enrich these products with PUFA) to enable the desired healthy diet.

The problem of the PUFAs is, that they have strong tendency to oxidise. This results in a loss of the PUFAs in the product and secondly (even worse) in the development of a strong and very unpleasant smell.

With increasing number of double bonds, the PUFAs are subject to increasing oxidative degradation and development of undesirable "off-flavours", mainly fishy and rancid smell and taste. Volatile degradation products cause off-flavour even at very low concentration. Sensory properties of a product may become unacceptable even before a loss of PUFAs can be detected analytically.

Another issue arises because PUFAs are oils compounds and therefore the incorporation of PUFA is not so easy and usually needs an emulsification step.

Now it was found that when PUFA salts (usually Na, K, or Ca salts) are used instead of PUFA very stable and easy to handle solid formulations are obtained.

By the term "solid formulation", it is meant that the formulation is in form. It is usually in the form of a powder, granule or beadlets. These formulations differ in the size of their particles.

Surprisingly it was found out that when at least one PUFA salt is embedded in a matrix comprising a casein phosphopeptide (CPP) a very stable solid formulation is obtained.

Therefore, the present invention relates to a solid formulation (SF) comprising
(i) at least one PUFA salt, and
(ii) a casein phosphopeptide.

As stated above the solid formulation can have various particles sizes.

When the solid formulation is a spray dried powder form the preferred average particle size of the solid formulation is 10-200 μm.

When the solid formulation is a beadlet, the preferred average particle size of the beadlet is 200-1000 μm.

When the solid formulation is a granule/pellet the preferred average particle size of the granule/pellet is preferably below 1000 μm.

The particle size is determined by using well-known methods, such as (scanning) electron microscopy. The particle size in the context of the present invention is defined as the longest dimension of a particle (such i.e. the diameter in case of spherical particle).

All particle sizes are determined by laser diffraction technique using a "Mastersizer 3000" of Malvern Instruments Ltd., UK. Further information on this particle size characterization method can e.g. be found in "Basic principles of particle size analytics", Dr. Alan Rawle, Malvern Instruments Limited, Enigma Business Part, Grovewood Road, Malvern, Worcestershire, WR14 1XZ, UK and the "Manual of Malvern particle size analyzer". Particular reference is made to the user manual number MAN 0096, Issue 1.0, November 1994. If nothing else is stated all particle sizes referring are Dv50 values (volume diameter, 50% of the population resides below this point, and 50% resides above this point) determined by laser diffraction. The particle size can be determined in the dry form.

Therefore, the present invention relates to a solid formulation (SF1) comprising
(i) at least one PUFA salt, and
(ii) a casein phosphopeptide,
wherein the average particle size is 10-200 μm.

Therefore, the present invention relates to a solid formulation (SF1') comprising
(i) at least one PUFA salt, and
(ii) a casein phosphopeptide,
wherein the average particle size is 200-1000 μm.

Therefore the present invention relates to a solid formulation (SF1") comprising
(i) at least one PUFA salt, and
(ii) a casein phosphopeptide,
wherein the average particle size is above 1000 μm.

The PUFAs are classified according to the position of the double bonds in the carbon chain of the molecule as n-9, n-6 or n-3 PUFAs. Examples of n-6 PUFAs are linoleic acid (C18:2), arachidonic acid (C20:4), γ-linolenic acid (GLA, C18:13) and dihomo-γ-linolenic acid (DGLA, C20:3). Examples of n-3 PUFAs are α-linolenic acid (C18:13), eicosapentaenoic acid (EPA, C20:5), and docosahexaenoic acid (DHA, C22:6). Especially EPA and DHA have attracted interest of the food industry in recent years. The most available sources of these two fatty acids are fish and the marine oils extracted from them. Suitable PUFA salts are the sodium, potassium, magnesium and/or calcium salts. Mixed salts are also suitable.

Very suitable PUFA oils are commercially available for example from DSM Nutritional Products Ltd. These suitable PUFA oils are MEG-3® 4020 EE Oil, MEG-3® 4030 EE Oil, MEG-3® 4421 EE Oil and MEG-3® 5020 EE Oil, which are then transformed into the salts.

Therefore, the present invention relates to a solid formulation (SF2), which is solid formulation (SF), (SF1), (SF1') or (SF1"), wherein the PUFA salts are the sodium, potassium, magnesium and/or calcium salts.

Therefore, the present invention relates to a solid formulation (SF3), which is solid formulation (SF), (SF1), (SF1'), (SF1") or (SF2), wherein the PUFA salts are chosen from the group consisting of linoleic acid, arachidonic acid, γ-linolenic acid, dihomo-γ-linolenic acid, α-linolenic acid, eicosapentaenoic acid, and docosahexaenoic acid in form of its sodium, potassium and/or calcium salts. The most available sources of these two fatty acids are fish and the marine oils extracted from them. Suitable PUFA salts are the sodium, potassium, magnesium and/or calcium salts. Mixed salts are also suitable.

The content of the PUFA salts can vary and it is usually at least 5 weight-% (wt-%), based on the total weight of the solid formulation.

Usually the PUFA salt (or mixture of PUFA salts) are present in an amount of up to 80 wt-%, based on the total weight of the solid formulation.

Preferably, the solid formulation according to the present invention comprises 10-70 wt-%, based on the total weight of the solid formulation, of at least one PUFA salt.

More preferably, the solid formulation according to the present invention comprises 20-60 wt-%, based on the total weight of the solid formulation, of at least one PUFA salt.

Therefore, the present invention relates to a solid formulation (SF4), which is solid formulation (SF), (SF1), (SF1'), (SF1"), (SF2) or (SF3), wherein the solid formulation comprises 5-80 wt-%, based on the total weight of the solid formulation, of at least one PUFA salt.

Therefore, the present invention relates to a solid formulation (SF5), which is solid formulation (SF), (SF1), (SF1'), (SF1"), (SF2), (SF3) or (SF4), wherein the solid formulation comprises 10-70 wt-%, based on the total weight of the solid formulation, of at least one PUFA salt.

More preferably, the solid formulation according to the present invention comprises 20-80 wt-%, based on the total weight of the solid formulation, of at least one PUFA salt.

The solid formulation according to the present also comprises casein phosphopeptide (CPP).

CPP is usually prepared from solubilized milk protein. It derived from the tryptic hydrolysis of casein. The peptides were phosphoseryl rich, which could bind divalent metal. The presence of phosphate groups originating from phosphorylated serine residues in close proximity to the peptide chain creates a polar, acidic domain that is favourable for sequestering divalent metals such as calcium, zinc, copper, manganese and iron. The presence of an anionic triplet (SerP-SerP-SerP-Glu-Glu) embedded in the bioactive peptide is a distinctive feature for all functional CPP derived from whole β-casein-4P (1-25), αs1-casein-5P (59-79), αs2-casein-4P (1-21) and αs2-casein-4P (46-70).

CPP is also commercially available. It is available i.e. under the tradename Hyvital® Casein Phosphopeptides from FrieslandCampina Domo.

The content of the CPP salts can vary and it is usually at least 10 wt-%, based on the total weight of the solid formulation.

Usually the CPP is present in an amount of up to 75 wt-%, based on the total weight of the solid formulation.

Furthermore, the present invention relates to a solid formulation comprising 10-75 wt-%, based on the total weight of the solid formulation, of CPP.

Furthermore, the present invention relates to a solid formulation comprising 15-70 wt-%, based on the total weight of the solid formulation, of CPP.

Therefore, the present invention relates to a solid formulation (SF6), which is solid formulation (SF), (SF1), (SF1'), (SF1"), (SF2), (SF3), (SF4) or (SF5), wherein the solid formulation comprising 10-75 wt-%, based on the total weight of the solid formulation, of CPP.

Therefore, the present invention relates to a solid formulation (SF7), which is solid formulation (SF), (SF1), (SF1'), (SF1"), (SF2), (SF3), (SF4), (SF5) or (SF6), wherein the solid formulation comprising 15-70 wt-%, based on the total weight of the solid formulation, of CPP.

All percentage in the context of the present invention are always added up to 100% in each solid formulation. In case the PUFA salts(s) and the CPP do not add up to 100% there is at least one other ingredient present.

Furthermore, the solid formulation according to the present invention can also comprise further ingredients.

A preferred group of such ingredients are gums, such as xanthan gum, gum arabic, gum ghatti, agar, alginic acid, sodium alginate, carrageenan, gum tragacanth, karaya gum, guar gum, locust bean gum or gellan gum.

These gums can even improve further improve the stability of the solid formulations according to the present invention.

A very preferred gum is gum Arabic.

Preferably, the solid formulation comprises up to 30 wt-%, based on the total weight of the solid formulation, of at least one gum.

More preferably, the solid formulation comprises up to 30 wt-%, based on the total weight of the solid formulation, of at least one gum chosen from the group consisting of xanthan gum, gum arabic, gum ghatti, agar, alginic acid, sodium alginate, carrageenan, gum tragacanth, karaya gum, guar gum, locust bean gum or gellan gum. Even more preferably, the solid formulation comprises up to 30 wt-%, based on the total weight of the solid formulation, of gum arabic.

Therefore, the present invention relates to a solid (SF8), which is solid formulation (SF), (SF1), (SF1'), (SF1"), (SF2), (SF3), (SF4), (SF5), (SF6) or (SF7), wherein the solid formulation comprises up to 30 wt-%, based on the total weight of the solid formulation, of at least one gum.

Therefore, the present invention relates to a solid formulation (SF8'), which is solid formulation (SF8), wherein the solid formulation comprises up to 30 wt-%, based on the total weight of the solid formulation, of at least one gum chosen from the group consisting of xanthan gum, gum arabic, gum ghatti, agar, alginic acid, sodium alginate, carrageenan, gum tragacanth, karaya gum, guar gum, locust bean gum or gellan gum.

Therefore, the present invention relates to a solid formulation (SF8"), which is solid formulation (SF8), wherein the solid formulation comprises up to 30 wt-%, based on the total weight of the solid formulation, of gum arabic.

Another preferred group of such ingredients are sugar alcohols (also called polyhydric alcohols, polyalcohols, alditols or glycitols).

Suitable sugar alcohols are for example glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol and polyglycitol.

Very preferred sugar alcohols are mannitol or maltitol.

Preferably, the solid formulation comprises up to 30 wt-%, based on the total weight of the solid formulation, of at least sugar alcohol.

More preferably, the solid formulation comprises up to 30 wt-%, based on the total weight of the solid formulation, of at least one sugar alcohol chosen from the group consisting of glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol and polyglycitol.

Even more preferably, the solid formulation comprises up to 30 wt-%, based on the total weight of the solid formulation, of mannitol and/or maltitol.

Therefore, the present invention relates to a solid (SF9), which is solid formulation (SF), (SF1), (SF1'), (SF1"), (SF2), (SF3), (SF4), (SF5), (SF6), (SF7), (SF8), (SF8') or (SF8"), wherein the solid formulation comprises up to 30 wt-%, based on the total weight of the solid formulation, of at least one sugar alcohol.

Therefore, the present invention relates to a solid formulation (SF9'), which is solid formulation (SF9), wherein the solid formulation comprises up to 30 wt-%, based on the total weight of the solid formulation, of at least one sugar alcohol from the group consisting of glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol and polyglycitol.

Therefore, the present invention relates to a solid formulation (SF9"), which is solid formulation (SF9), wherein the solid formulation comprises up to 30 wt-%, based on the total weight of the solid formulation, of mannitol and/or maltitol.

Furthermore, the solid formulation according to the present invention can further comprise at least one auxiliary agent, wherein the auxiliary agent is chosen from the group consisting of antioxidants (such as ascorbic acid or salts thereof, tocopherol (synthetic or natural); butylated hydroxytoluene (BHT); butylated hydroxyanisole (BHA); propyl gallate; tert. butyl hydroxyquinoline, ascorbic acid esters of a fatty acid and/or ethoxyquin), plasticisers, stabilisers, humectants, protective colloids, dyes, fragrances, fillers and buffers.

These auxiliary agents can be present in an amount of up to 30 wt-%, based on the total weight of the solid formulation.

Therefore the present invention relates to a solid (SF10), which is solid formulation (SF), (SF1), (SF1'), (SF1"), (SF2), (SF3), (SF4), (SF5), (SF6), (SF7), (SF8), (SF8'), (SF8"), (SF9), (SF9') or (SF9"), wherein the solid formulation comprises at least one auxiliary agent, wherein the auxiliary agent is chosen from the group consisting of antioxidants (such as ascorbic acid or salts thereof, tocopherol (synthetic or natural); butylated hydroxytoluene (BHT); butylated hydroxyani-sole (BHA); propyl gallate; tert. butyl hydroxyquinoline, ascorbic acid esters of a fatty acid and/or ethoxyquin), plasticisers, stabilisers, humectants, protective colloids, dyes, fragrances, fillers and buffers.

Therefore, the present invention relates to a solid (SF10'), which is solid formulation (SF10), wherein the solid formulation comprises up to 30 wt-%, based on the total weight of the solid formulation of at least one auxiliary agent.

The shape of the particles of the solid formulation according to the present invention is not an essential feature of the present invention. The shape can be sphere-like or any other form (also mixtures of shapes). Usually and preferably, the particles are sphere-like.

One of the main advantages of the solid formulations according to the present invention also lies in the production of the solid formulation.

No emulsification step is needed.

All ingredients are dissolved in water and then usually spray dried. Other drying techniques like spray granulation or beadlet process may be applied as well.

The process of production of the solid formulation is usually the following
 (i) the water-soluble ingredients of the matrix are mixed in their dry form and then dissolved in water; afterwards
 (ii) the PUFA salt is added, afterwards
 (iii) the mixture is (spray) dried.

It is also possible that all water-soluble ingredients are solved in water (and not mixed in dry form).

Depending on the temperature of the spray drying process, the solid formulation can still comprise water (usually not more than 5 wt-%, based on the total weight of the solid formulation).

The solid formulation (SF), (SF1), (SF1'), (SF1"), (SF2), (SF3), (SF4), (SF5), (SF6), (SF7), (SF8), (SF8'), (SF8"), (SF9), (SF9'), (SF9"), (SF10) or (SF10') can also be used as such or used to be incorporated into other product forms.

The solid formulation can be incorporated into food, feed, pharmaceutical and/or personal care products.

The solid formulation can be also being incorporated into a premix. This premix is then incorporated into a food, feed, pharmaceutical and/or personal care product.

Another embodiment of the present invention is the use of at least one casein phosphopeptide for manufacturing a solid formulation comprising at least one PUFA salt.

The solid formulation according to the present invention can also be used in pharmaceutical products. The pharmaceutical product can be in any galenical form, usually in the form of tablets.

A further embodiment of the present invention relates to food products, feed products, dietary supplements, and/or pharmaceutical products, comprising at least one solid formulation (SF), (SF1), (SF1'), (SF1"), (SF2), (SF3), (SF4), (SF5), (SF6), (SF7), (SF8), (SF8'), (SF8"), (SF9), (SF9'), (SF9"), (SF10) and/or (SF10').

The invention is illustrated by the following Examples. All temperatures are given in ° C. and all parts and percentages are related to the weight.

General

All the solid formulations, which were tested, are produced using the procedure described in Example 1. The ingredients and/or their concentration vary, not the process parameters.

The salts (Na or K) of the following commercially available PUFA oils (available from DSM Nutritional Products Ltd) have been used MEG-3® 4020 EE Oil (This s a marine omega-3 long chain polyunsaturated fatty acid. This ethyl ester has a minimum of 360 mg EPA, 180 mg DHA, and 590 mg total Omega-3 per gram).

MEG-3® 4030 EE Oil (this is a marine omega-3 long chain polyunsaturated fatty acid. This ethyl ester has a minimum of 360 mg EPA, 270 mg DHA, and 680 mg total Omega-3 per gram.)

MEG-3® 4421 EE Oil is a marine omega-3 long chain polyunsaturated fatty acid. This ethyl ester has a minimum of 400 mg EPA, 200 mg DHA, and 650 mg total Omega-3 per gram.

MEG-3® 5020 EE Oil is a marine omega-3 long chain polyunsaturated fatty acid. This ethyl ester has a minimum of 460 mg EPA, 180 mg DHA, and 700 mg total Omega-3 per gram

EXAMPLE 1

25 g of maltodextrin (maltodextrin 28-31), 20 g of sodium ascorbate and 80 g of casein phosphopeptide (Hyvital® Casein Phosphopetide from FrieslandCampina Domo) were put (in their dry state) into a beaker and mixed well.

Afterward 800 g of water were added slowly to this mixture under constant stirring. This solution was heated up to 50° C., and adjust the pH was adjusted (by NaOH or KOH) to 8.5.

The PUFA salt (the Na salt of MEG-3® 4030 EE Oil) was also heated up to 50° C. and then the warm PUFA salt was added to the aqueous solution. A slurry way obtained.

The so obtained slurry was spray dried (using a GEA MOBILE MINOR™), inlet temperature was set at 150~180° C., outlet temperature was controlled around 60~80° C.

A free-flowing powder was obtained.

Testing of the Solid Formulations

The storage stability of the produced solid formulations was tested as follows:

The solid formulations were stored at room temperature and after defined storage times the formulations were evaluated by a sensory panel of experienced and well-trained persons.

Each person of this panel sniffed at the solid formulations and gave them a value of the sensory scale.

This sensory scale, which was applied, has values that goes from 0 to 15. 0 means no smell 15 means extremely strong.

The following compositions are tested (the amount of the ingredients is given in gram (g)):

TABLE 1

Formulations (1-4). The formulation 1 is the one produced as in Example 1. The forms 2-4 are comparative examples produced according to the method of example 1.

| Ingredients | Form 1 | Form 2 | Form 3 | Form 4 |
| --- | --- | --- | --- | --- |
| PUFA Na Salt of MEG-3 ® 4030 EE Oil | 250 | 250 | 250 | 250 |
| Maltodextrin 28-31 | 25 | 25 | 25 | 25 |
| Sodium Ascorbate | 15 | 15 | 15 | 15 |
| Casein Phosphopeptide | 80 | | | |
| Gelatin Rousselot 175 | | 80 | | |
| Whey Protein Concentrate | | | 80 | |
| Egg Yolk | | | | 80 |
| Water | 1000 | 1000 | 1000 | 1000 |

Form 1 is the inventive formulation. The Forms 2, 3, and 4 are comparative examples using other (commonly used) matrix materials Sensory Results:

TABLE 2 the sensory results of the forms 1-4

| | | Fishy Marine Complex | Other off |
| --- | --- | --- | --- |
| FORM 1 | initial | — | — |
| | 4 weeks | — | — |
| | 8 weeks | — | — |
| | 12 weeks | 1.0 | — |
| | 16 weeks | — | — |
| | 20 weeks | — | — |
| FORM 2 | initial | 4.0 | |
| | 4 weeks | 4.0 | |
| | 8 weeks | 5.0 | |
| FORM 3 | initial | 2.5 | |
| | 4 weeks | 3.0 | |
| | 8 weeks | 3.0 | |
| FORM 4 | initial | 5.0 | |
| | 4 weeks | 2.0 | |
| | 8 weeks | 3.0 | |

The formulations using other matrix materials are showing an unpleasant smell ("fishy smell") right from the start!

Formulations 5 and 6:

The formulations are produced in accordance with the process as disclosed in Example 1.

TABLE 3 formulations 5 and 6

| Ingredients | Form 5 | Form 6 |
| --- | --- | --- |
| PUFA K Salt of MEG-3 ® 4421 EE Oil | 250 | 250 |
| Maltodextrin 28-31 | 25 | 25 |
| Sodium Ascorbate | 20 | 20 |
| Casein Phosphopeptide | 80 | 50 |
| TIC Pretested ® Gum Arabic Spray Dry Powder - Grade #1 | | 30 |
| Water | 1000 | 1000 |

These two forms (Form 5 and Form 6) are solid formulations according to the invention.

Sensory Results

TABLE 4 sensory results of formulations 5 and 6

| | | Fishy Marine Complex | Other Off |
| --- | --- | --- | --- |
| FORM 5 | initial | 1.0 | |
| | 4 weeks | | 0.5 |
| | 8 weeks | | 2 |
| | 12 weeks | | |
| | 16 weeks | | |
| | 20 weeks | | 1 |
| | 24 weeks | | |
| | 36 weeks | | 0.8 |
| FORM 6 | initial | 1.0 | |
| | 4 weeks | | 0.5 |
| | 8 weeks | | |
| | 12 weeks | | |
| | 16 weeks | | 1 |
| | 20 weeks | 1.0 | 1 |
| | 24 weeks | | 2.0 |
| | 36 weeks | | 1.5 |

Formulations 7 and 8:

TABLE 5 formulations 7 and 8

| Ingredient | Form 7 | Form 8 |
| --- | --- | --- |
| PUFA Na Salt of MEG-3 ® 4421 EE Oil | 250 | 250 |
| Maltodextrin 28-31 | 25 | 25 |
| Sodium Ascorbate | 20 | 20 |
| Casein Phosphopeptide | 25 | 25 |
| TIC Pretested ® Gum Arabic Spray Dry Powder - Grade #1 | 30 | 30 |
| Mannitol | 25 | |
| Maltitol | | 25 |
| Water | 1000 | 1000 |

Sensory Results

TABLE 6 sensory results of formulations 7 and 8

| | | Fishy Marine Complex | Other Off |
| --- | --- | --- | --- |
| Form 7 | initial | | 1 |
| | 4 weeks | | 1.3 |
| | 8 weeks | | |
| | 12 weeks | | 0.8 |
| | 16 weeks | | 2.0 |
| | 20 weeks | 1.5 | 1.5 |
| | End | | |

TABLE 6-continued sensory results of formulations 7 and 8

|  |  | Fishy Marine Complex | Other Off |
|---|---|---|---|
| Form 8 | initial |  |  |
|  | 4 weeks |  |  |
|  | 8 weeks |  |  |
|  | 12 weeks | 2.0 |  |
|  | 16 weeks |  |  |
|  | 20 weeks |  |  |
|  | 24 weeks |  |  |
|  | 36 weeks |  |  |

It can be seen from these evaluation tests that the solid formulations according to the present invention are better significantly than such, which are produced with a different (commonly and widely used) matrix material.

The invention claimed is:

1. A particulate solid formulation comprising:
   (i) at least one polyunsaturated fatty acid (PUFA) salt, and
   (ii) 10-75 wt. % of a casein phosphopeptide.

2. The particulate solid formulation according to claim 1, wherein particles of the solid formulation have an average particle size (Dv50) of 10-200 μm.

3. The particulate solid formulation according to claim 1, wherein particles of the solid formulation have an average particle size (Dv50) of 200-1000 μm.

4. The particulate solid formulation according to claim 1, wherein particles of the solid formulation have an average particle size (Dv50) of more than 1000 μm.

5. The particulate solid formulation according to claim 1, wherein the PUFA salt comprises at least one PUFA salt selected from the group consisting of PUFA sodium salts, PUFA potassium salts, PUFA magnesium salts and PUFA calcium salts.

6. The particulate solid formulation according to claim 1, wherein the at least one PUFA salt is selected from the group consisting of sodium, potassium and/or calcium salts of linoleic acid, arachidonic acid, γ-linolenic acid, dihomo-γ-linolenic acid, α-linolenic acid, eicosapentaenoic acid, and docosahexaenoic acid.

7. The particulate solid formulation according to claim 1, wherein the solid formulation comprises 5-80 wt. %, based on total weight of the solid formulation, of the at least one PUFA salt.

8. The particulate solid formulation according to claim 1, wherein the solid formulation comprises up to 30 wt. %, based on total weight of the solid formulation, of at least one gum.

9. The particulate solid formulation according to claim 1, wherein the solid formulation comprises up to 30 wt. %, based on total weight of the solid formulation, of at least one sugar alcohol.

10. The particulate solid formulation according to claim 1, wherein the solid formulation comprises at least one auxiliary agent selected from the group consisting of antioxidants, plasticisers, stabilisers, humectants, protective colloids, dyes, fragrances, fillers and buffers.

11. The particulate solid formulation according to claim 10, wherein the antioxidant is at least one selected from the groups consisting of ascorbic acid or salts thereof, synthetic tocopherol, natural tocopherol, butylated hydroxytoluene, butylated hydroxyanisole, propyl gallate; tert. butyl hydroxyquinoline and ascorbic acid esters of a fatty acid and ethoxyquin.

12. The particulate solid formulation according to claim 10, wherein the humectant is at least one selected from the group consisting of glycerine, sorbitol and polyethylene glycol.

13. A process for production of the particulate solid formulation of claim 1, wherein the process comprises:
   (i) dry mixing water soluble matrix ingredients to form a dry matrix mix,
   (ii) dissolving the dry matrix mix in water to form an aqueous matrix solution;
   (iii) adding the at least one PUFA salt to the aqueous matrix solution to form an aqueous mixture of the at least on PUFA salt and the matrix solution; and thereafter
   (iv) spray drying the aqueous mixture of the at least on PUFA salt and the matrix solution to form the particles of the solid formulation.

14. Food products, feed products, dietary supplements, pharmaceutical products and/or premixes, comprising the at least one solid formulation according to claim 1.

* * * * *